United States Patent
Miller et al.

(10) Patent No.: US 10,603,041 B2
(45) Date of Patent: Mar. 31, 2020

(54) CIRCULAR SURGICAL STAPLER WITH ANGULARLY ASYMMETRIC DECK FEATURES

(71) Applicant: Ethicon Endo-Surgery, LLC, Guaynabo, PR (US)

(72) Inventors: Christopher C. Miller, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 425 days.

(21) Appl. No.: 15/350,624

(22) Filed: Nov. 14, 2016

(65) Prior Publication Data

US 2018/0132854 A1    May 17, 2018

(51) Int. Cl.
| | | |
|---|---|---|
| *A61B 17/115* | (2006.01) | |
| *A61B 17/068* | (2006.01) | |
| *A61B 17/072* | (2006.01) | |
| *A61B 17/11* | (2006.01) | |

(52) U.S. Cl.
CPC ........ *A61B 17/1155* (2013.01); *A61B 17/068* (2013.01); *A61B 17/072* (2013.01); *A61B 17/07207* (2013.01); *A61B 17/1114* (2013.01); *A61B 2017/07221* (2013.01); *A61B 2017/07271* (2013.01); *A61B 2017/07278* (2013.01)

(58) Field of Classification Search
CPC ... A61B 17/155; A61B 17/1155; A61B 17/10; A61B 2017/07271
USPC .......................................... 227/179.1, 180.1
See application file for complete search history.

(56) References Cited

U.S. PATENT DOCUMENTS

| | | | |
|---|---|---|---|
| 5,122,156 A * | 6/1992 | Granger | A61B 17/115 227/179.1 |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,282,810 A * | 2/1994 | Allen | A61B 17/115 606/150 |
| 5,285,945 A | 2/1994 | Brinkerhoff et al. | |

(Continued)

FOREIGN PATENT DOCUMENTS

| | | |
|---|---|---|
| EP | 1 316 290 A2 | 6/2003 |
| EP | 3 225 180 A1 | 10/2017 |

OTHER PUBLICATIONS

European Search Report, Extended, and Written Opinion dated Mar. 6, 2018 for Application No. EP 17201276.7, 9 pgs.

(Continued)

*Primary Examiner* — Alexander M Valvis
*Assistant Examiner* — Daniel Jeremy Leeds
(74) *Attorney, Agent, or Firm* — Frost Brown Todd LLC

(57) ABSTRACT

An apparatus includes a body, a shaft assembly, a stapling head assembly, and an anvil. The stapling head assembly includes a deck member, a plurality of staples, and a driver. The deck member includes a first deck surface, a second deck surface, an outer annular array of staple openings formed through the deck surfaces, an inner annular array of staple openings formed through the deck surfaces, and a plurality of stand-off features extending distally from the second deck surface. The second deck surface is recessed relative to the first deck surface. The driver is operable to drive the staples through the staple openings. The anvil is operable to compress tissue against the deck surface.

20 Claims, 15 Drawing Sheets

(56) References Cited

U.S. PATENT DOCUMENTS

| | | | |
|---|---|---|---|
| 5,292,053 A | 3/1994 | Bilotti et al. | |
| 5,333,773 A | 8/1994 | Main et al. | |
| 5,350,104 A | 9/1994 | Main et al. | |
| 5,360,154 A * | 11/1994 | Green | A61B 17/115 227/179.1 |
| 5,533,661 A | 7/1996 | Main et al. | |
| 7,794,475 B2 | 9/2010 | Hess et al. | |
| 8,157,152 B2 * | 4/2012 | Holsten | A61B 17/00491 227/176.1 |
| 8,328,062 B2 * | 12/2012 | Viola | A61B 17/115 227/179.1 |
| 8,413,870 B2 | 4/2013 | Pastorelli et al. | |
| 8,657,176 B2 * | 2/2014 | Shelton, IV | A61B 17/00491 227/178.1 |
| 8,733,613 B2 * | 5/2014 | Huitema | A61B 17/07207 227/176.1 |
| 8,905,977 B2 * | 12/2014 | Shelton | A61B 17/07207 604/131 |
| 8,910,847 B2 | 12/2014 | Nalagatla et al. | |
| 9,010,609 B2 * | 4/2015 | Carter | A61B 17/07292 227/176.1 |
| 9,033,204 B2 * | 5/2015 | Shelton, IV | A61B 17/1155 227/179.1 |
| 9,232,945 B2 * | 1/2016 | Zingman | A61B 17/072 |
| 9,289,207 B2 | 3/2016 | Shelton, IV | |
| 9,364,233 B2 | 6/2016 | Alexander, III et al. | |
| 9,463,022 B2 | 10/2016 | Swayze et al. | |
| 9,498,222 B2 | 11/2016 | Chin | |
| 9,532,783 B2 | 1/2017 | Swayze et al. | |
| 9,572,573 B2 | 2/2017 | Scheib et al. | |
| 9,597,075 B2 * | 3/2017 | Shelton, IV | A61B 17/1114 |
| 9,597,081 B2 * | 3/2017 | Swayze | A61B 17/1155 |
| 9,603,594 B2 * | 3/2017 | Milliman | A61B 17/0686 |
| 9,801,626 B2 * | 10/2017 | Parihar | A61B 17/115 |
| 9,987,001 B2 * | 6/2018 | Williams | A61B 17/068 |
| 2003/0178465 A1 * | 9/2003 | Bilotti | A61B 17/115 227/180.1 |
| 2005/0245965 A1 * | 11/2005 | Orban, III | A61B 17/115 606/214 |
| 2007/0175963 A1 * | 8/2007 | Bilotti | A61B 17/115 227/179.1 |
| 2010/0108740 A1 * | 5/2010 | Pastorelli | A61B 17/1114 227/178.1 |
| 2010/0170932 A1 * | 7/2010 | Wenchell | A61B 17/068 227/176.1 |
| 2011/0011916 A1 * | 1/2011 | Levine | A61B 17/115 227/179.1 |
| 2012/0168487 A1 * | 7/2012 | Holsten | A61B 17/00491 227/176.1 |
| 2012/0241491 A1 * | 9/2012 | Aldridge | A61B 17/07292 227/175.1 |
| 2012/0241505 A1 * | 9/2012 | Alexander, III | A61B 17/00491 227/179.1 |
| 2012/0325893 A1 * | 12/2012 | Pastorelli | A61B 17/072 227/177.1 |
| 2013/0026209 A1 | 1/2013 | Mozdzierz et al. | |
| 2014/0144968 A1 * | 5/2014 | Shelton, IV | A61B 17/1114 227/175.1 |
| 2014/0151430 A1 | 6/2014 | Scheib et al. | |
| 2014/0158747 A1 | 6/2014 | Measamer et al. | |
| 2014/0166728 A1 | 6/2014 | Swayze et al. | |
| 2014/0197225 A1 * | 7/2014 | Penna | A61B 17/068 227/179.1 |
| 2014/0309665 A1 * | 10/2014 | Parihar | A61B 17/1155 606/139 |
| 2015/0014393 A1 * | 1/2015 | Milliman | A61B 90/98 227/180.1 |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2015/0136831 A1 * | 5/2015 | Baxter, III | A61B 17/0644 227/176.1 |
| 2015/0297233 A1 * | 10/2015 | Huitema | A61B 17/068 227/176.1 |
| 2016/0100837 A1 | 4/2016 | Huang et al. | |
| 2016/0374666 A1 | 12/2016 | DiNardo et al. | |
| 2016/0374672 A1 | 12/2016 | Bear et al. | |
| 2017/0086822 A1 * | 3/2017 | Scheib | A61B 17/1155 |
| 2017/0086847 A1 * | 3/2017 | DiNardo | A61B 17/068 |
| 2017/0086848 A1 * | 3/2017 | Miller | A61B 17/07207 |
| 2017/0258471 A1 * | 9/2017 | DiNardo | A61B 17/068 |
| 2017/0281189 A1 * | 10/2017 | Nalagatla | A61B 17/0644 |
| 2018/0125495 A1 * | 5/2018 | Sgroi, Jr. | A61B 17/1155 |
| 2018/0132848 A1 * | 5/2018 | Miller | A61B 17/07207 |

OTHER PUBLICATIONS

International Search Report and Written Opinion dated Aug. 4, 2017 for Application No. PCT/US2017/035121, 9 pgs.
U.S. Appl. No. 14/864,310, filed Sep. 24, 2015.
U.S. Appl. No. 15/350,513, filed Nov. 14, 2016.
U.S. Appl. No. 15/350,593, filed Nov. 14, 2016.
U.S. Appl. No. 15/350,621, filed Nov. 14, 2016.

\* cited by examiner

CIRCULAR SURGICAL STAPLER WITH ANGULARLY ASYMMETRIC DECK FEATURES

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
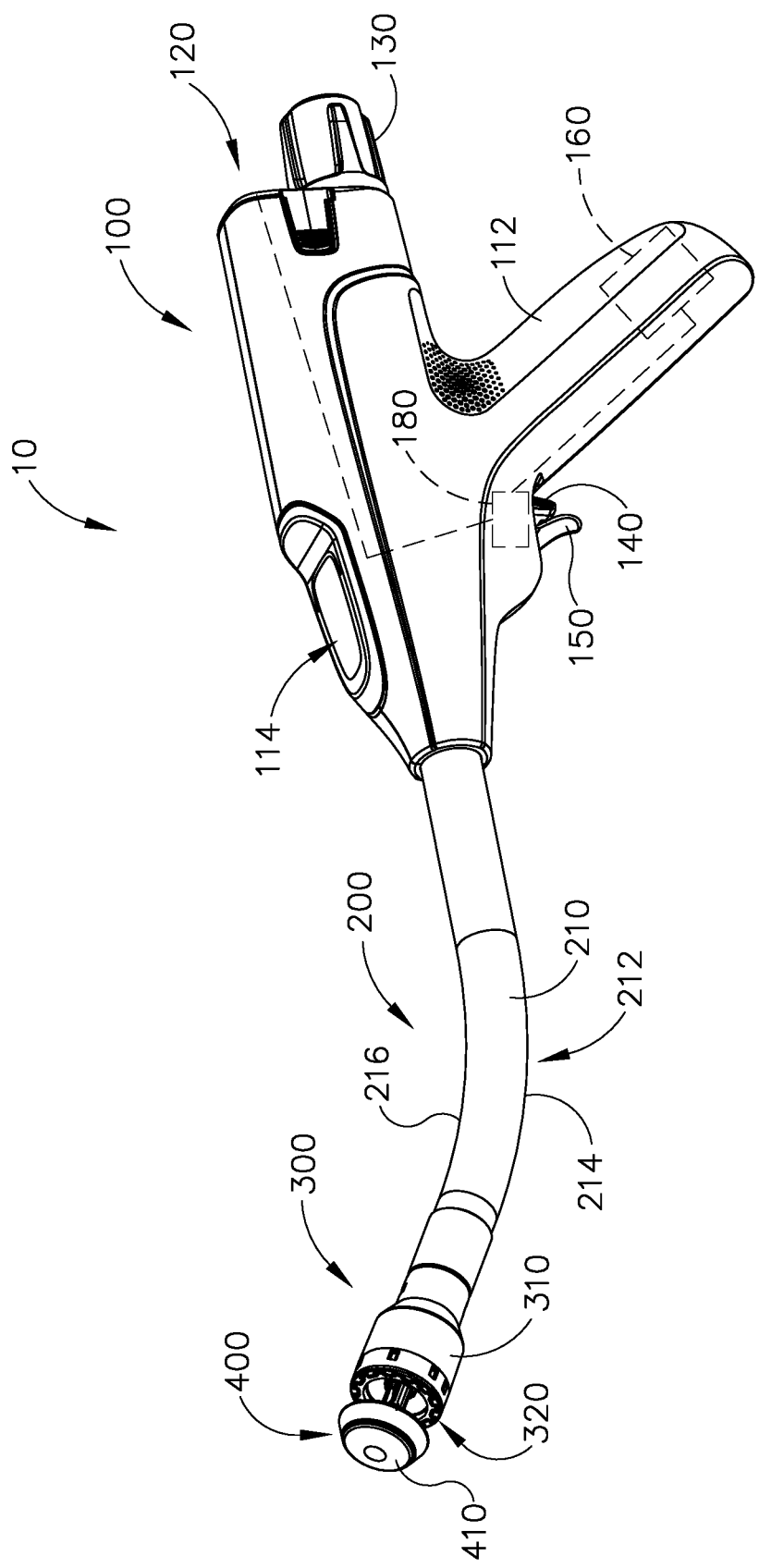
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
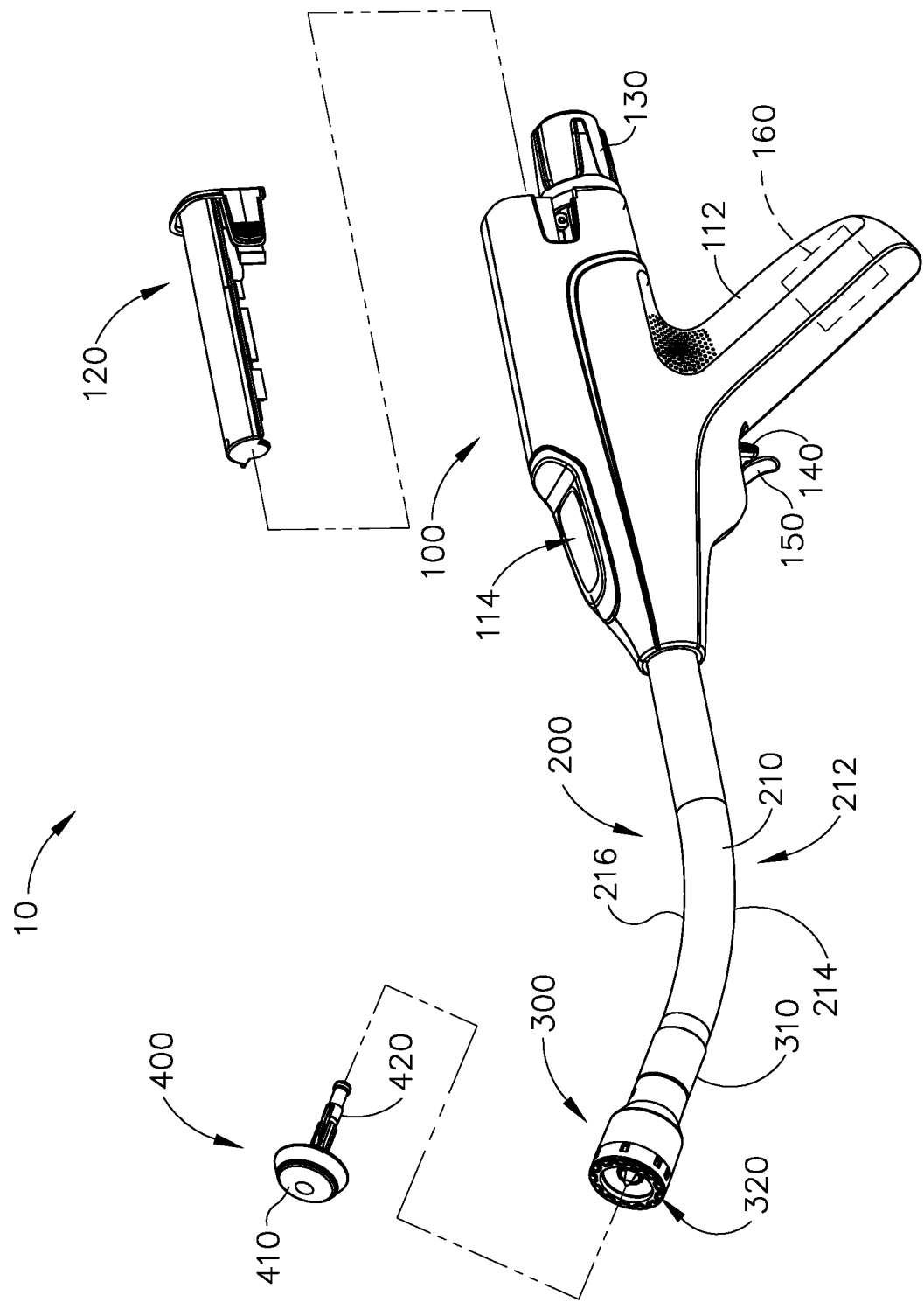
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189, on Nov. 19, 2019; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
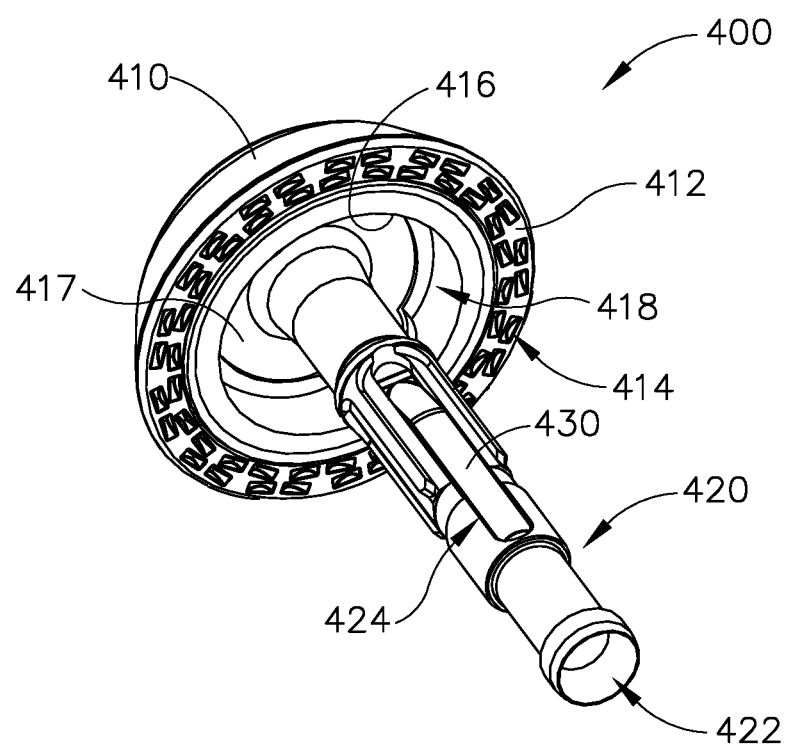
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
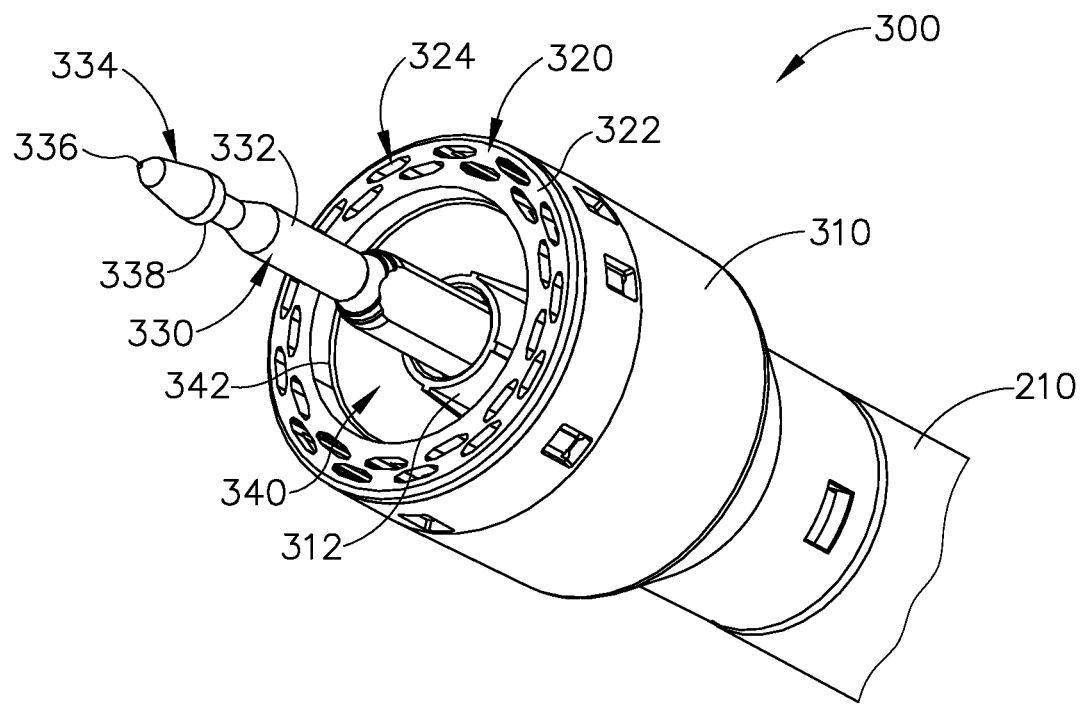
FIG. 4 depicts a perspective view of the stapling head assembly of the circular stapler of FIG. 1.
Figure 5:
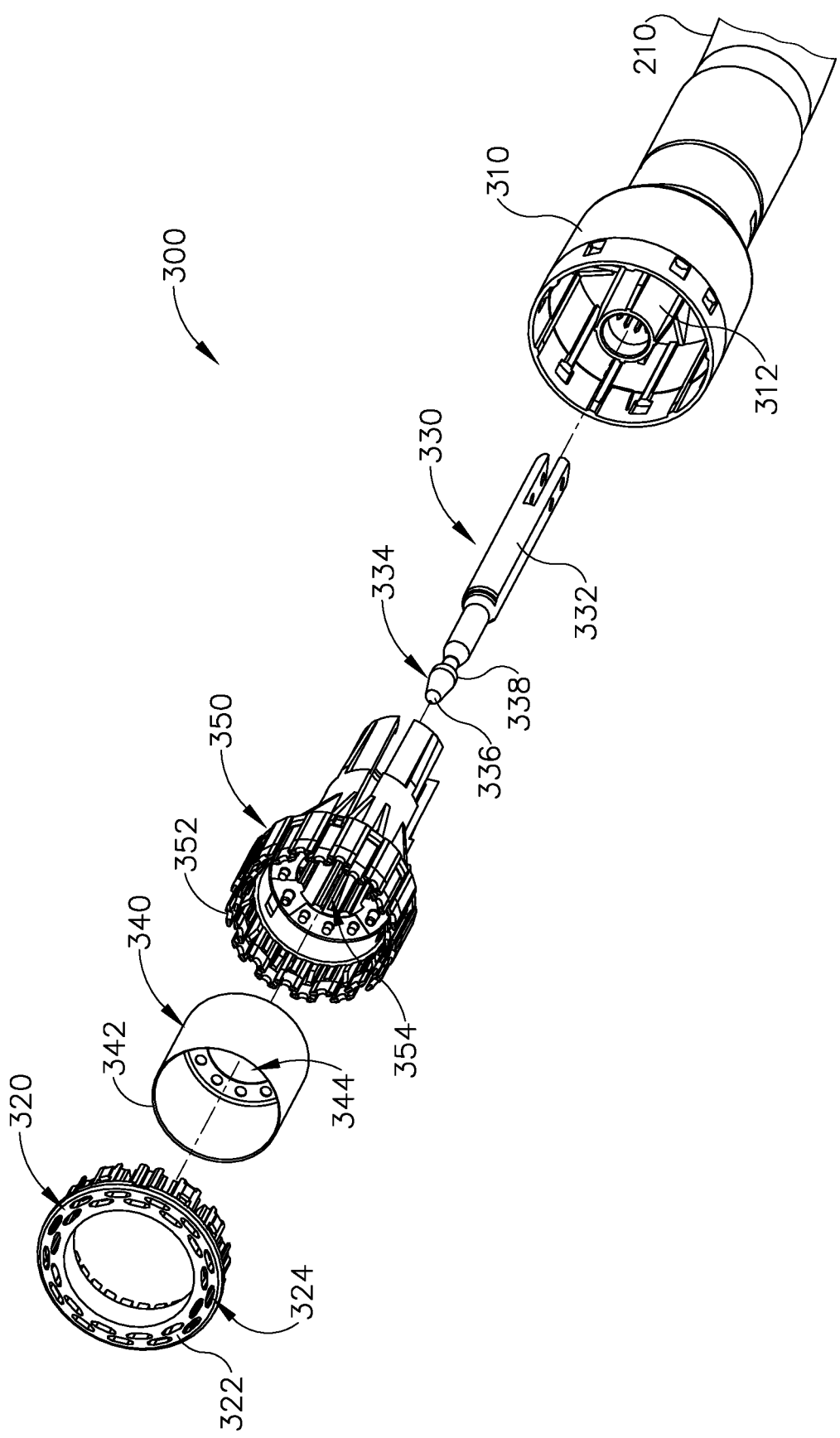
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
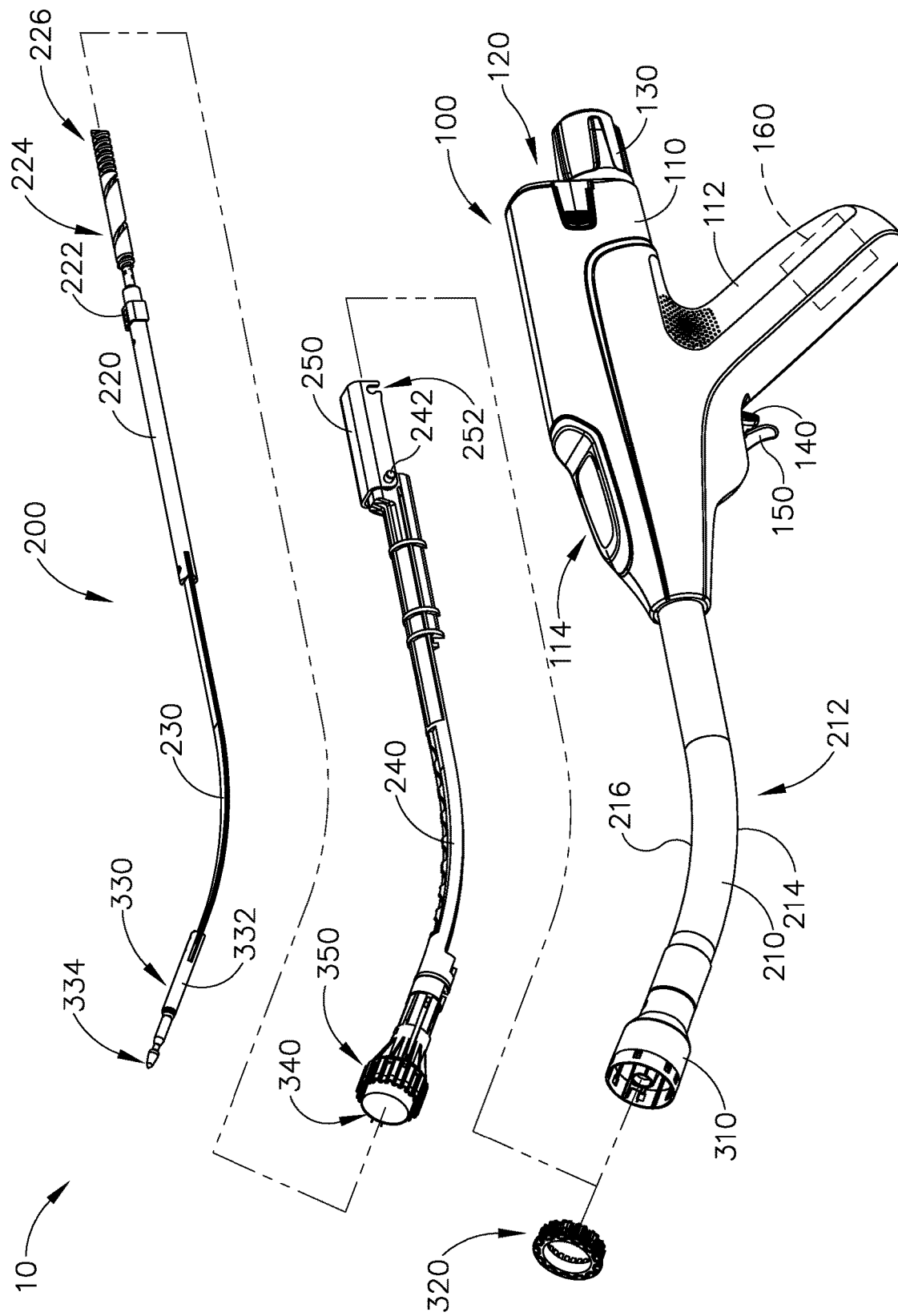
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling assembly (300). The operator may thus observe user feedback feature (114) while rotating knob (130), to confirm whether the suitable gap distance between anvil (400) and stapling assembly (300) has been achieved. By way of example only, user feedback feature (114) may be configured and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019, the disclosure of which is incorporated by reference herein. Other suitable forms of providing user feedback will be apparent to those of ordinary skill in the art in view of the teachings herein.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, issued as U.S. Pat. No. 10,456,134 on Oct. 29, 2019, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
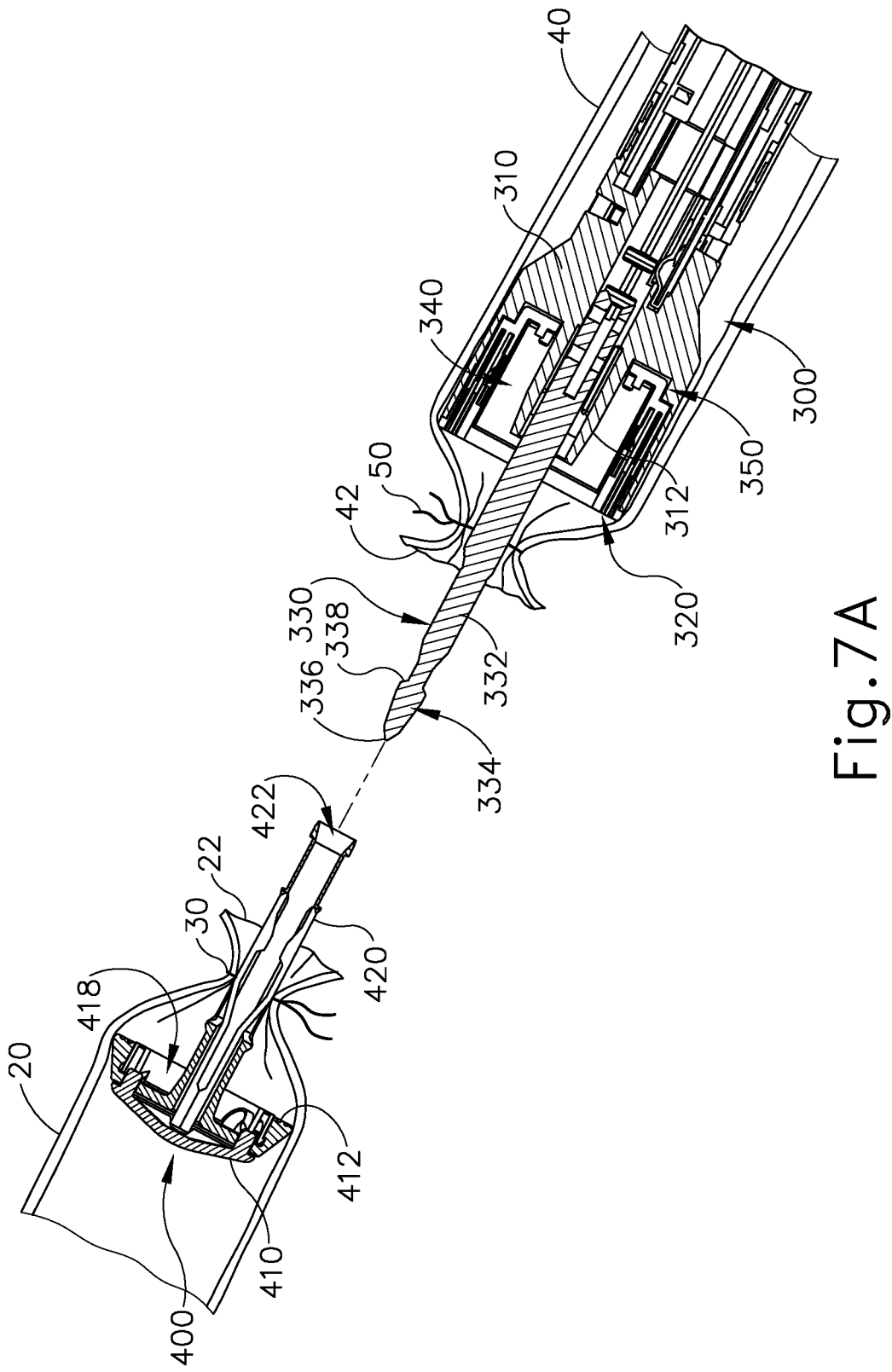
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically in accordance with at least some of the teachings of U.S. Pub. No. 2016/0100837, entitled "Surgical Stapling Apparatus Comprising a Tissue Stop," published Apr. 14, 2016, issued as U.S. Pat. No. 10,076,325 on Sep. 18, 2018, the disclosure of which is incorporated by reference herein; and/or U.S. patent application Ser. No. 14/864,310, entitled "Apparatus and Method for Forming a Staple Line with Trocar Passageway," filed Sep. 24, 2015, issued as U.S. Pat. No. 10,485,548 on Nov. 26, 2019, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
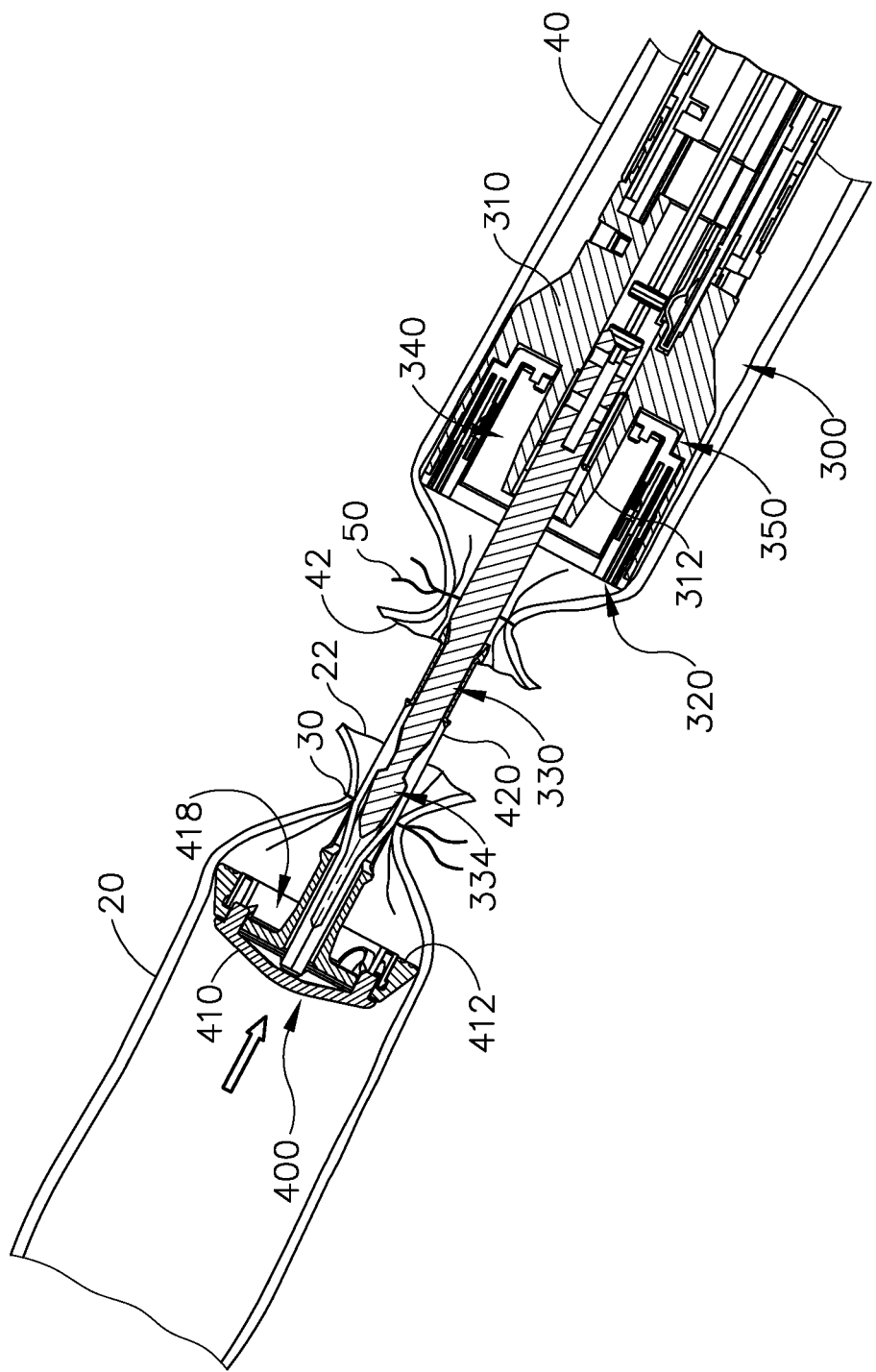
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
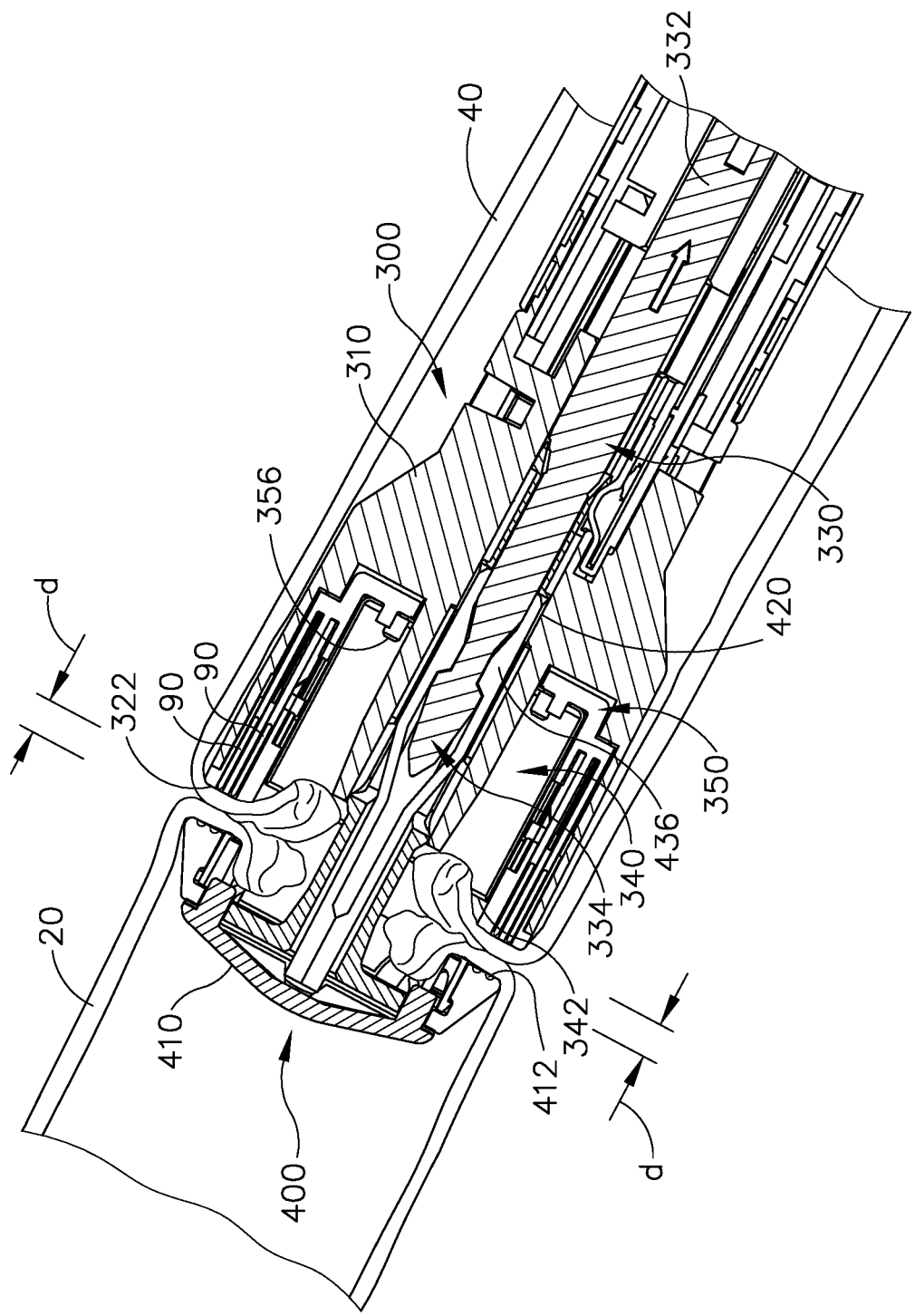
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 7D:
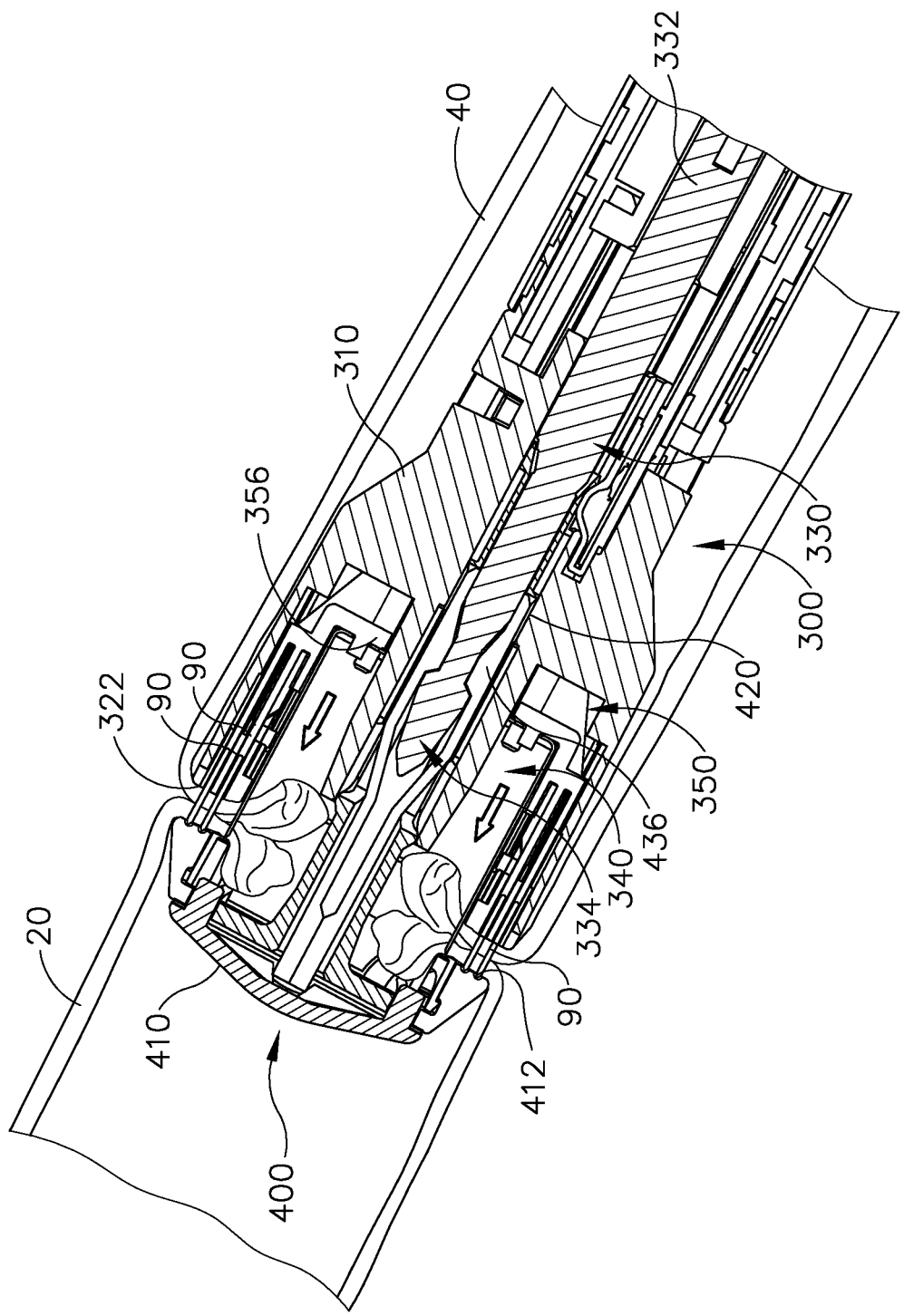
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 7E:
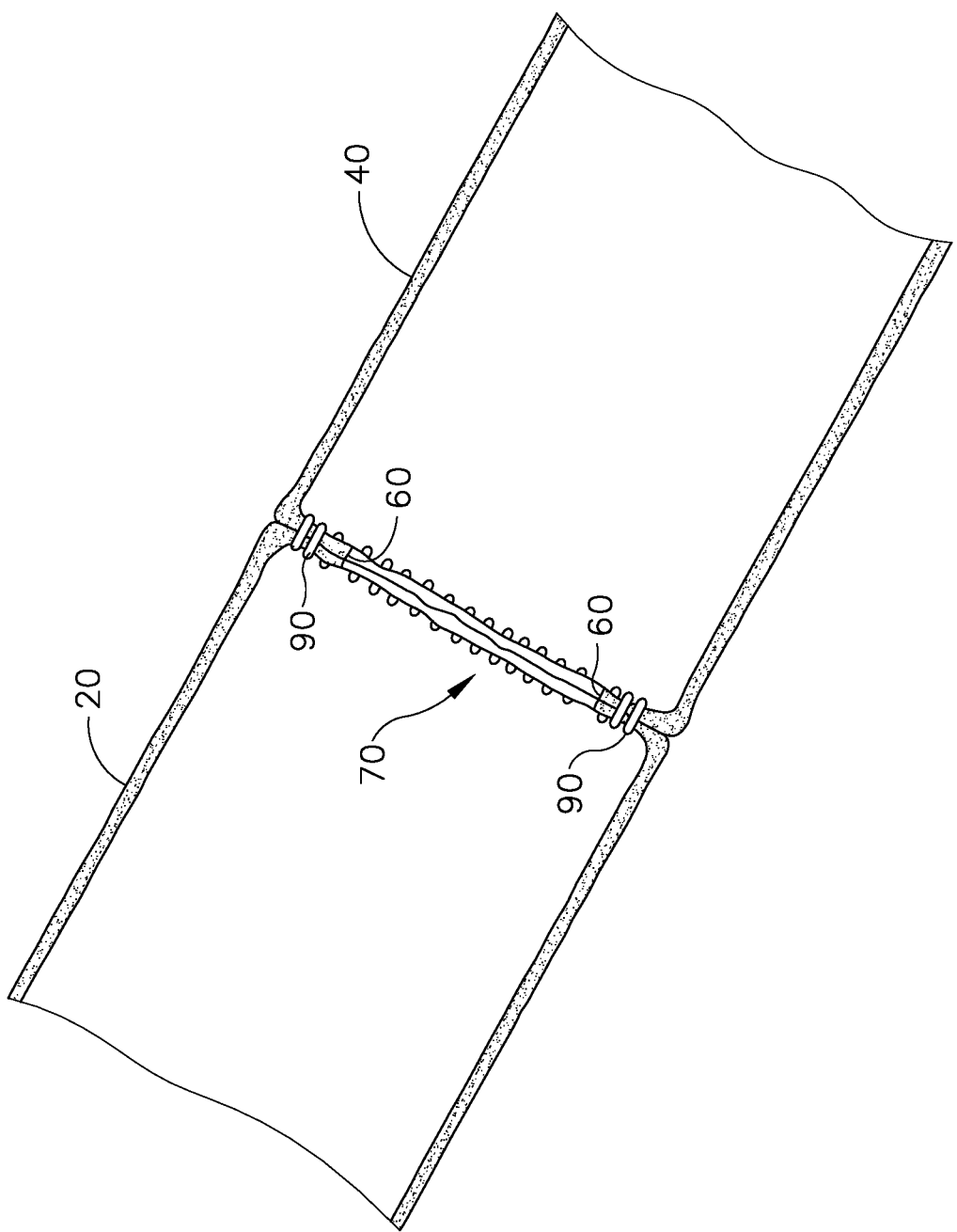
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130)

to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Alternative Stapling Head Assembly

Figure 8:
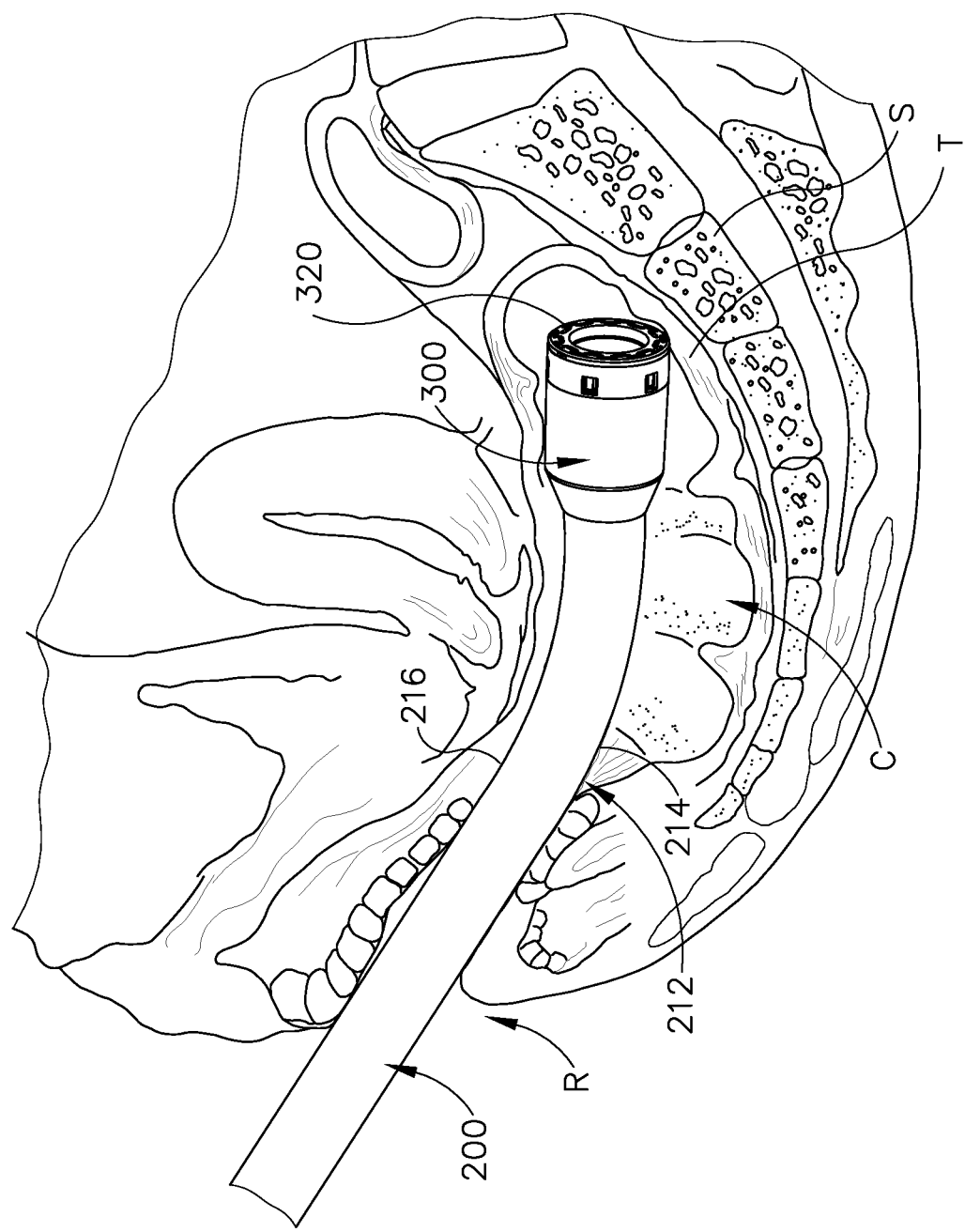
FIG. 8 depicts a partial perspective view of the stapling head assembly and shaft assembly of the circular stapler of FIG. 1 inserted in a patient's colon, with the stapling head assembly positioned near the patient's sacrum, and with the patient's anatomy shown in cross-section.

As noted above, in some instances, anatomical structures (20, 40) may comprise sections of a patient's colon. FIG. 8 shows stapling head assembly (300) and a distal portion of shaft assembly (200) disposed in a patient's colon (C). As shown, stapling head assembly (300) and shaft assembly (200) are inserted via the patient's rectum (R). As also shown, the curvature of curved section (212) is configured to generally complement the curvature of the patient's colon (C). Nevertheless, as also shown in FIG. 8, there may be instances where deck member (320) tends to compress tissue (T) of the patient's colon (C) against the patient's sacrum (S) and/or some other substantially rigid anatomical structure. Depending on the angle at which the operator has inserted stapling head assembly (300) and shaft assembly (200), and/or depending on the force that the operator is applying to stapling head assembly (300) and shaft assembly (200) during insertion, the tissue (T) of the patient's colon (C) may become damaged (e.g., torn) when the tissue (T) is pinched between stapling head assembly (300) and the patient's sacrum (S). In versions where deck member (320) has tissue gripping features and/or other protruding features (e.g., staple guidance features, etc.), such features may increase the risk of damage to the tissue (T) of the patient's colon (C) as stapling head assembly (300) and shaft assembly (200) are being inserted into the patient's colon (C).

Figure 9:
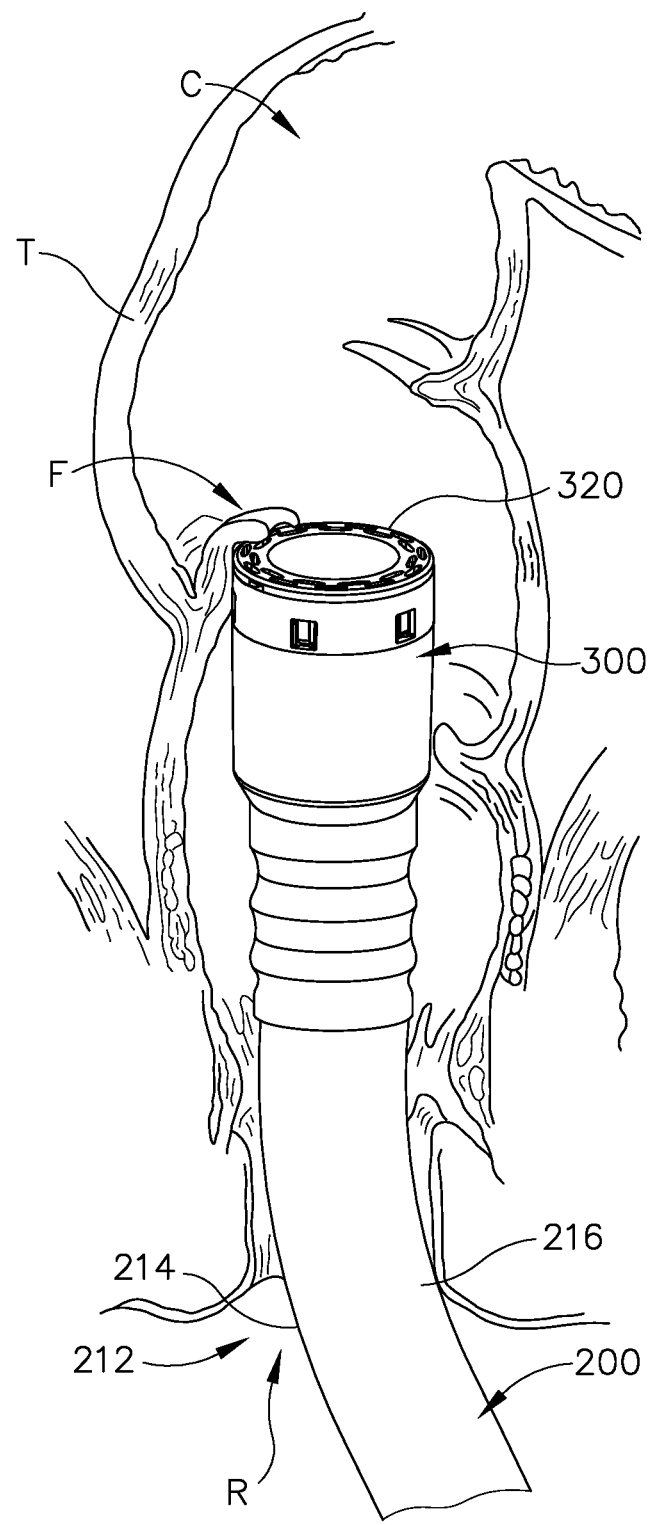
FIG. 9 depicts a partial perspective view of the stapling head assembly and shaft assembly of the circular stapler of FIG. 1 inserted in a patient's colon, with the stapling head assembly engaging a fold of the colon tissue, and with the patient's anatomy shown in cross-section.

Similarly, as shown in FIG. 9, those of ordinary skill in the art will recognize that the tissue (T) of the colon (C) defines a plurality of folds (F), and that stapling head assembly (300) may get snagged on such folds (F) as stapling head assembly (300) and shaft assembly (200) are inserted in the patient's colon (C). This snagging may also create a risk of damaging the tissue (T) of the patient's colon (C). Again, in versions where deck member (320) has tissue gripping features and/or other protruding features (e.g., staple guidance features, etc.), such features may increase the risk of damage to the tissue (T) of the patient's colon (C) as stapling head assembly (300) gets snagged on folds (F).

It may therefore be desirable to provide a version of stapling head assembly (300) that minimizes the risk of damaging the tissue (T) of the patient's colon (C) during insertion of stapling head assembly (300) and shaft assembly (200) into the patient's colon (C). Moreover, it may be desirable to provide a version of stapling head assembly (300) that includes features that enhance gripping of tissue during actuation of stapling head assembly (300), thereby promoting successful tissue cutting and staple deployment, without increasing the risk of damaging the tissue (T) of the patient's colon (C) during insertion of stapling head assembly (300) and shaft assembly (200) into the patient's colon (C).

Figure 10:
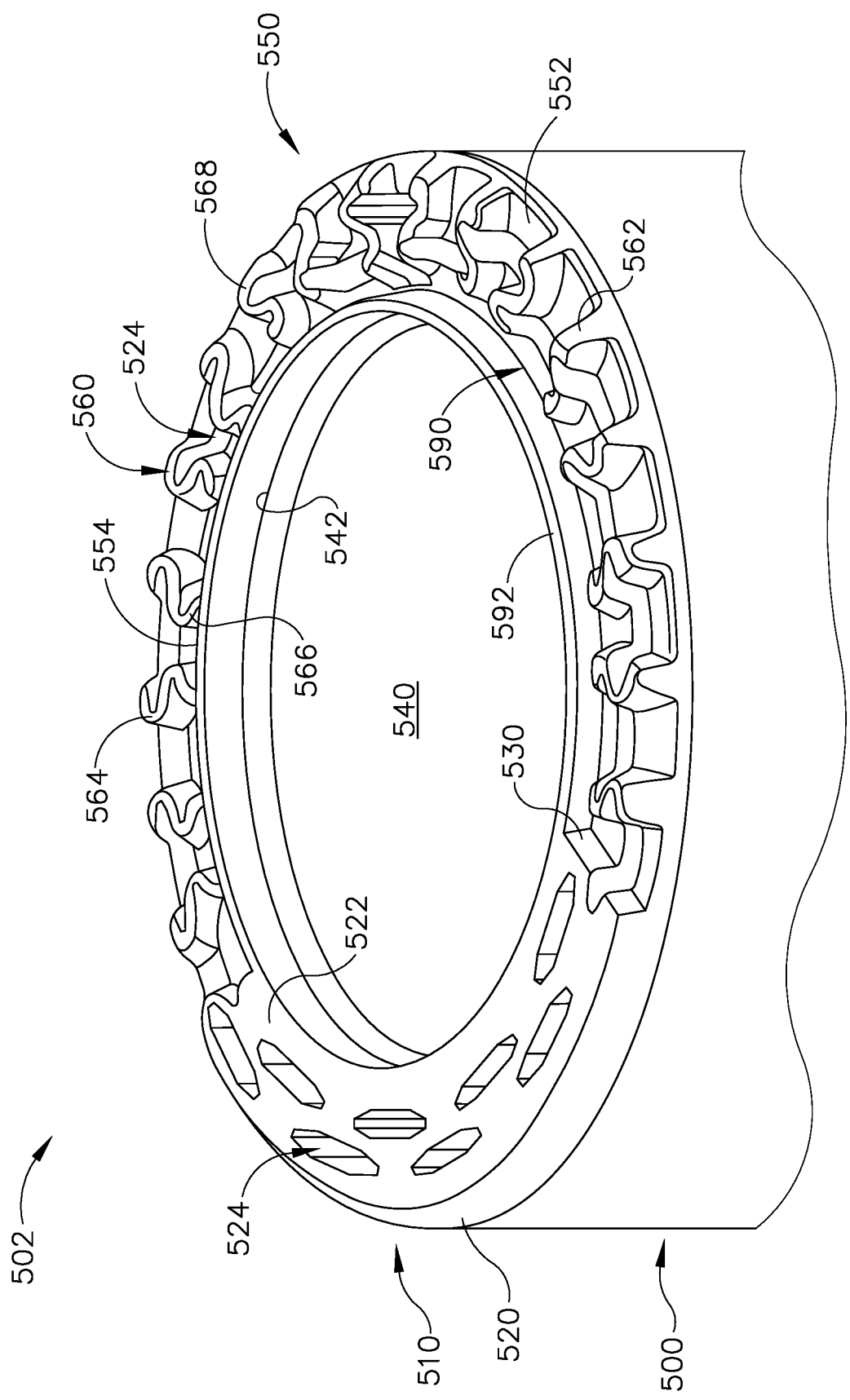
FIG. 10 depicts a perspective view of an exemplary alternative stapling head assembly that may be incorporated into the circular stapler of FIG. 1.

FIG. 10 shows an exemplary alternative stapling head assembly (500) that may be readily incorporated into stapling instrument in place of stapling head assembly (300). Except as otherwise described below, stapling head assembly (500) of this examine is configured and operable just like stapling head assembly (300) described above. Stapling head assembly (500) of this example includes a deck member (502) having a deck surface (522) that defines two concentric annular arrays of staple openings (524). Staple openings (524) are arranged to correspond with the arrangement of staple drivers (352) and staple forming pockets (414) described above. Thus, each staple opening (524) is configured to provide a path for a corresponding staple driver (352) to drive a corresponding staple through deck member (500) and into a corresponding staple forming pocket (414) when stapling head assembly (500) is actuated. Deck member (502) defines an inner diameter that is just slightly larger than the outer diameter defined by knife member (540). Deck member (502) is thus configured to allow knife member (540) to translate distally to a point where cutting edge (542) is distal to deck surface (522).

Unlike deck member (320) described above, deck member (502) of the present example includes a first zone (510) and a second zone (550). First zone (510) is characterized in that deck surface (522) is substantially flat within first zone (510). First zone (510) includes an outer edge (520) that has a curved configuration. Outer edge (520) is thus configured to reduce the risk of outer edge (520) snagging on tissue (T) as stapling head assembly (500) is inserted into the patient's colon (C).

Second zone (550) is characterized in that second zone has a recessed deck surface (552) with a plurality of stand-off features (560) protruding upwardly from recessed deck surface (552). A stepped transition (530) is formed at the boundaries between zones (510, 550), thereby providing a step-down from deck surface (522) to recessed deck surface (552). In some versions, transition (530) is oriented perpendicularly relative to surfaces (522, 552), such that transition (530) provides a steep drop-off from deck surface (522) to recessed deck surface (552). In some other versions, transition (530) is oriented obliquely relative to surfaces (522, 552), such that transition (530) provides a sloped transition from deck surface (522) to recessed deck surface (552). Alternatively, transition (530) may have a curved configuration or any other suitable configuration.

Stand-off features (560) each include an outwardly facing surface (562), an outer wall portion (564), and an inner wall portion (566). Outwardly facing surfaces (562) are curved to complement the curved configuration of outer edge (520). Outwardly facing surfaces (562) are thus configured to reduce the risk of stand-off features (560) snagging on tissue (T) as stapling head assembly (500) is inserted into the patient's colon (C). Outer wall portions (564) are configured to wrap partially around the outer array of staple openings (524). Outer wall portions (564) are thus configured and positioned to provide guidance to staples (90) exiting the outer array of staple openings (524). Inner wall portions (564) are configured to wrap partially around the inner array of staple openings (524). Inner wall portions (564) are thus configured and positioned to provide guidance to staples (90) exiting the inner array of staple openings (524).

Since each inner wall portion (566) is contiguous with a corresponding outer wall portion (564), and since the inner array of staple openings (524) is angularly offset from the outer array of staple openings (524), each stand-off feature (560) generally has a zig-zag configuration. In the present example, the upper edges (568) of stand-off features (560)

are located on the same plane as deck surface (522), such that upper edges (568) and deck surface (522) will contact tissue along the same plane. In other words, while recessed deck surface (552) is recessed relative to upper edges (568), deck surface (522) is not recessed relative to upper edges (568). In some other versions, at least a portion of upper edges (568) extends above or below the plane of deck surface (522).

It should also be understood that stand-off features (560) are discretely formed in the present example, such that gaps are located between each stand-off feature (560) and the adjacent stand-off features (560). In some other versions, stand-off features (560) are contiguous with each other.

Second zone (550) also includes an upwardly protruding annular wall (592). Annular wall (592) is flush with deck surface (522). Annular wall (592) is configured to compress a partially annular region of tissue against anvil (400), thereby providing assistance for edge (542) of knife member (540) to shear tissue. Annular wall (592) is contiguous and coplanar with the inner region of deck surface (522), such that annular wall (592) and deck surface cooperate to compress a fully annular region of tissue against anvil (400), providing even compression along a full circumference of a tissue region. An annular recess (590) is formed between annular wall (590) and stand-off features (560). In some other versions, inner wall portions (566) extend fully to annular wall (590), such that annular wall (590) is connected directly to stand-off features (560) via inner wall portions (566).

It should be understood that the protruding configuration of stand-off features (560) relative to recessed deck surface (552) will provide tissue engagement effects in second zone (550) are not provided in first zone (510). In particular, when tissue is compressed between deck member (502) and anvil (400) as described above, portions of the compressed tissue will enter the recessed areas adjacent to stand-off features (560). By having some of the tissue enter these recessed areas, this may reduce the total pressure that would otherwise be applied to the tissue if the tissue were being compressed against a consistently flat deck surface like deck surface (322). By reducing the total pressure on the tissue, deck member (502) may reduce the risk of the tissue from becoming fractured by over-compression. In addition to reducing the total pressure on tissue, the entry of tissue portions in recessed areas adjacent to stand-off features (560) may provide a grip on the compressed tissue that is greater than the grip that could otherwise be achieved using a consistently flat deck surface like deck surface (322). The enhanced grip of tissue may promote cleaner cutting by knife member (540) and also promote more successful deployment of staples (90) in the tissue. Thus, the presence of stand-off features (560) may both reduce the risk of over-compression of tissue and promote greater success in cutting and stapling the tissue.

Figure 11:
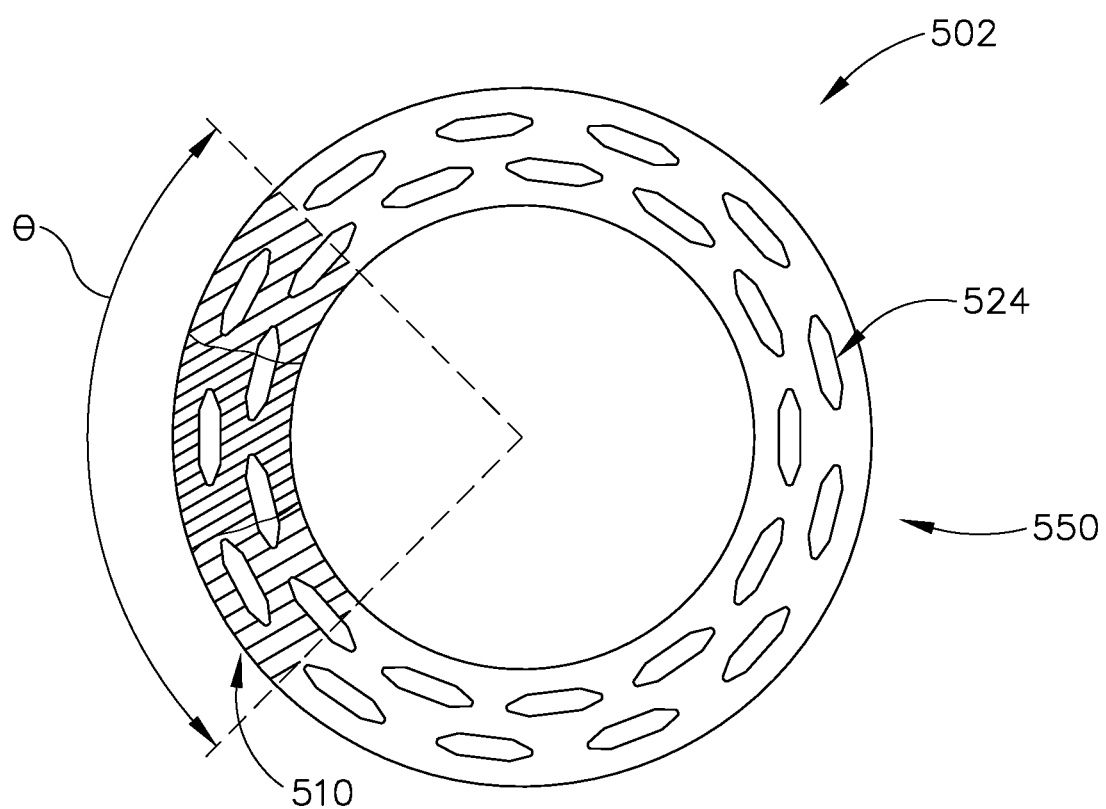
FIG. 11 depicts a top plan view of a deck member of the stapling head assembly of FIG. 10.

As best seen in FIG. 11, first zone (510) spans along an angular range (θ) of approximately 90° of the circumference of deck member (502) in the present example. By way of further example only, first zone (510) may span along an angular range (θ) of less than approximately 90° of the circumference of deck member (502). For instance, first zone (510) may span along an angular range (θ) between approximately 30° and approximately 90° of the circumference of deck member (502); or between approximately 45° and approximately 90° of the circumference of deck member (502).

As noted above, the entry of tissue into recessed areas adjacent to stand-off features (560) may reduce the risk of over-compression of tissue and promote greater success in cutting and stapling the tissue during actuation of anvil (400) and stapling head assembly (500). However, this same entry of tissue into recessed areas adjacent to stand-off features (560) may present some risks during insertion of stapling head assembly (500) and shaft assembly (200) into tissue. In other words, in variations of deck member (502) where stand-off features (560) are positioned along the full circumference of deck member (502), there may be a tendency for tissue (T) to enter the recessed areas adjacent to stand-off features (560) during insertion of shaft assembly (200) and a stapling head assembly (500) into the patient's colon (C). Any resulting snagging of tissue (T) on stand-off features (560) may increase the risk of damage to tissue (T) in the event that the tissue (T) is being pinched against the sacrum (S) as described above with reference to FIG. 8.

To avoid the above-noted risks that might otherwise be associated with tissue snagging on stand-off features (560) during insertion of shaft assembly (200) and stapling head assembly (500) into the patient's colon (C), first zone (510) is positioned to correspond with outer curve (214) of curved section (212) of shaft assembly (200). As shown in FIG. 8, the region of stapling head assembly (300) corresponding to outer curve (214) is the region of stapling head assembly (300) that would tend to pinch the tissue (T) against the sacrum (S). Thus, by having first zone (510) in this region, stapling head assembly (500) avoids the risks that might otherwise be associated with stand-off features (560) during insertion of shaft assembly (200) and stapling head assembly (500) into the patient's colon (C); while still providing the advantages of stand-off features (560) in second zone when anvil (400) and stapling head assembly (500) are actuated.

Figure 12:
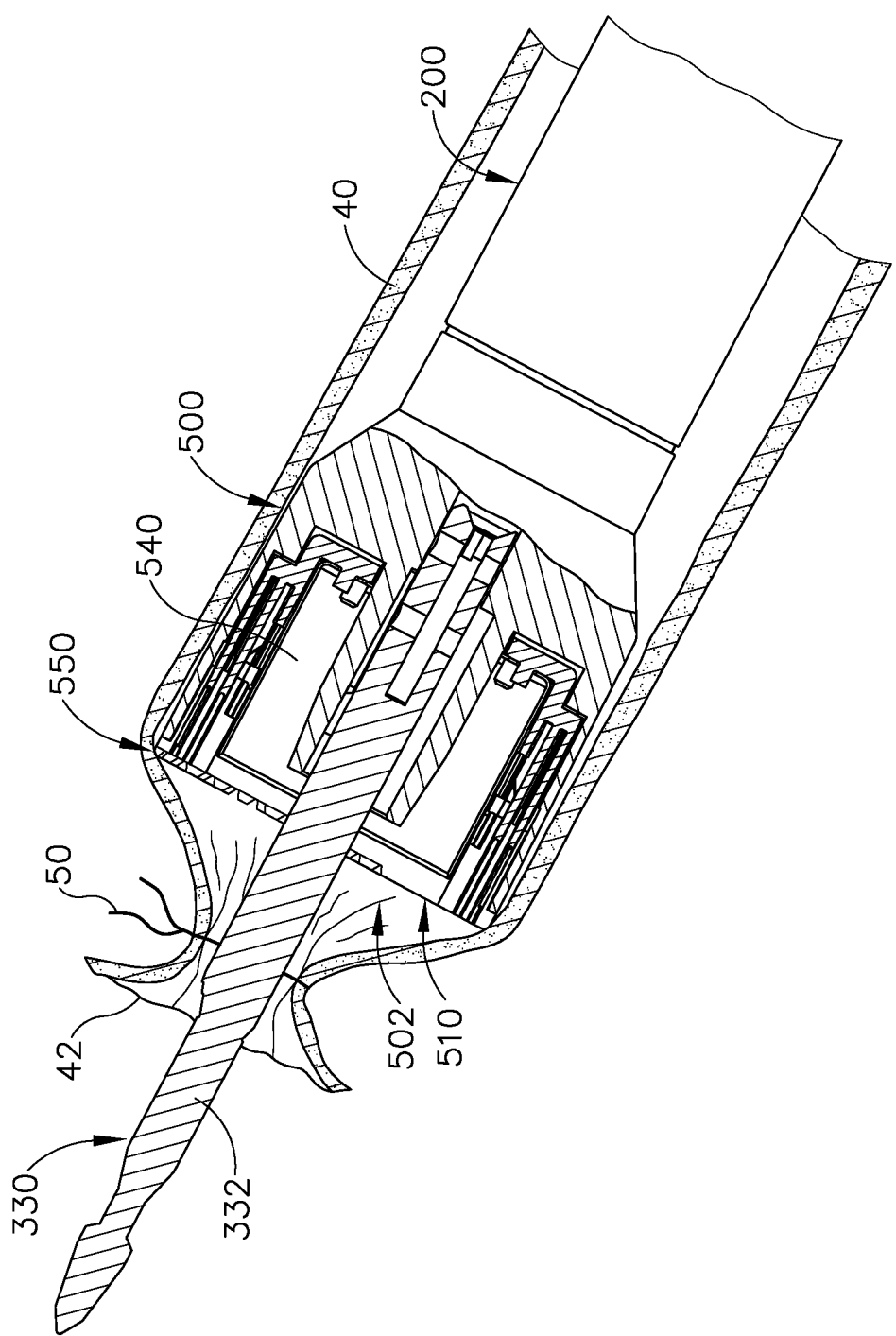
FIG. 12 depicts a partial cross-sectional view of the stapling head assembly of FIG. 10 positioned in a section of a digestive tract.

In addition to reducing the risk of damage to tissue (T) that might otherwise occur due to pinching of the tissue (T) against the sacrum (S), the configuration of deck member (502) may also provide a reduced risk of damage to tissue (T) when stapling head assembly (500) has arrived at a position where trocar (300) may be secured to anvil (400). FIG. 12 shows an example of stapling head assembly (500) in such a position. In particular, FIG. 12 shows stapling head assembly (500) positioned within tubular anatomical structure, with purse-string suture (50) is provided about a mid-region of shaft (332) to generally secure the position of stapling head assembly (500) in tubular anatomical structure (40). It should be understood that annular wall (592) is intentionally omitted from the view shown in FIG. 12, to demonstrate how upper edges (568) are flush with deck surface (522) in the present example. It should also be understood that annular wall (592) would also be flush with upper edges (568) in the present example, such that annular wall (592) would obscure the view of stand-off features (560) in FIG. 12 if upper annular wall (592) were not omitted from FIG. 12.

As can be seen, with stapling head assembly (500) in the position shown in FIG. 12, the outermost region of the distal end of stapling head assembly (500) is bearing against the bunched-up region of tissue of anatomical structure (40). In alternative versions where this outermost region of the distal end of stapling head assembly (500) presents a relatively sharp corner, such a corner may tend to damage or even tear this adjacent region of tissue. However, in the present example, since both outer edge (520) and outwardly facing surfaces (562) provide a curved profile, there is a reduced risk of tearing the annular region of tissue contacted by outer edge (520) and outwardly facing surfaces (562). Thus, even if the operator urges stapling head assembly (500) distally while stapling head assembly (500) is located in the position shown in FIG. 12, the curved configuration of the outermost region of the distal end of stapling head assembly (500) may substantially prevent the outermost region of the distal end of stapling head assembly (500) from tearing the adjacent tissue. While this region of stapling head assembly (500) (i.e., the region collectively defined by outer edge (520) and outwardly facing surfaces (562)) has a curved profile in this example, in some other versions this region of stapling head assembly (500) may have a chamfered profile or any other suitable kind of atraumatic profile.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly has a distal end; (c) a stapling head assembly located at the distal end of the shaft assembly, wherein the stapling head assembly comprises: (i) a deck member, wherein the deck member comprises: (A) a first deck surface, (B) a second deck surface, wherein the second deck surface is recessed relative to the first deck surface, (C) an outer annular array of staple openings formed through the first and second deck surfaces, (D) an inner annular array of staple openings formed through the first and second deck surfaces, and (E) a plurality of stand-off features extending distally from the second deck surface, (ii) a plurality of staples, and (iii) a driver operable to drive the staples through the staple openings; and (d) an anvil, wherein the anvil is operable to compress tissue against the deck surface.

Example 2

The apparatus of claim 1, wherein each stand-off feature partially encompasses an end of a corresponding staple opening of the outer annular array of staple openings.

Example 3

The apparatus of claim 1, wherein each stand-off feature partially encompasses an end of a corresponding staple opening of the inner annular array of staple openings.

Example 4

The apparatus of claim 1, wherein each stand-off feature comprises an outer wall portion and an inner wall portion, wherein the outer wall portion partially encompasses an end of a corresponding staple opening of the outer annular array of staple openings, wherein the inner wall portion partially encompasses an end of a corresponding staple opening of the inner annular array of staple openings.

Example 5

The apparatus of claim 4, wherein the outer wall portion and the inner wall portion of each stand-off feature forms a respective zig-zag configuration.

Example 6

The apparatus of claim 1, wherein each stand-off feature has a rounded outer edge having a curvature.

Example 7

The apparatus of claim 6, wherein the first deck surface has a rounded outer edge, wherein the rounded outer edge of the first deck surface has the same curvature as the curvature of the rounded outer edges of the stand-off features.

Example 8

The apparatus of claim 1, wherein each stand-off feature has an upper edge located along a plane, wherein the first deck surface is coplanar with the plane along with the upper edges of the stand-off features are located.

Example 9

The apparatus of claim 1, wherein the deck member further includes a step-down transition from the first deck surface to the second step surface.

Example 10

The apparatus of claim 1, wherein the deck member defines a first angular region and a second angular region, wherein the first deck surface extends along only the first angular region, wherein the second deck surface extends along only the second angular region.

Example 11

The apparatus of claim 10, wherein the first angular region extends along an angular range between approximately 30° and approximately 900 of a circumference of the deck member.

Example 12

The apparatus of claim 10, wherein the shaft assembly comprises a curved section including an inner curve and an outer curve.

Example 13

The apparatus of claim 12, wherein the first angular region is angularly positioned to correspond with the outer curve, wherein the second angular region is angularly positioned to correspond with the inner curve.

Example 14

The apparatus of claim 1, wherein the first deck surface is flat.

Example 15

The apparatus of claim 1, wherein the deck member further comprises an inner annular wall extending distally from the second deck surface.

Example 16

The apparatus of claim 15, wherein the inner annular wall has a distal edge that is coplanar with the first deck surface.

Example 17

The apparatus of claim 15, wherein the inner annular wall is spaced inwardly from the stand-off features such that a recess is defined between the inner annular wall and the stand-off features.

Example 18

An apparatus comprising a stapling head assembly, wherein the stapling head assembly comprises: (a) an annular deck member, wherein the annular deck member comprises: (i) a first deck surface extending along a first angular range of the annular deck member, (ii) a second deck surface extending along a second angular range of the annular deck member, (iii) an outer annular array of staple openings formed through the first and second deck surfaces, (iv) an inner annular array of staple openings formed through the first and second deck surfaces, (v) a plurality of tissue engagement features extending distally from or recessed within the second deck surface, and (vi) an inner annular wall extending distally from the second deck surface, wherein the inner annular wall is positioned inwardly from the tissue engagement features, (b) a plurality of staples; and (c) a driver operable to drive the staples through the staple openings.

Example 19

The apparatus of claim 18, wherein the second deck surface is recessed relative to the first deck surface.

Example 20

An apparatus comprising: (a) a shaft assembly extending distally from the body, wherein the shaft assembly comprises: (i) a proximal end, (ii) a distal end, and (iii) a curved section located between the proximal end and the distal end, wherein the curved section includes an inner curve and an outer curve; and (b) a stapling head assembly located at the distal end of the shaft assembly, wherein the stapling head assembly comprises: (i) a first deck surface having an angular extent positioned to correspond with the outer curve of the shaft assembly, (ii) a second deck surface having an angular extent positioned to correspond with the inner curve of the shaft assembly, (iii) an outer annular array of staple openings formed through the first and second deck surfaces, (iv) an inner annular array of staple openings formed through the first and second deck surfaces, (v) a plurality of tissue engagement features extending distally from or recessed within the second deck surface, (vi) a plurality of staples, and (vii) a driver operable to drive the staples through the staple openings.

IV. Miscellaneous

It should be understood that the teachings above may be readily combined with the teachings of U.S. patent application Ser. No. 15/350,513, entitled "Circular Surgical Stapler with Recessed Deck," filed Nov. 14, 2016, published as U.S. Pub. No. 2018/0132853 on May 17, 2018, the disclosure of which is incorporated by reference herein. Various suitable ways in which the teachings herein and the teachings of U.S. patent application Ser. No. 15/350,513 , filed on Nov. 14, 2016, published as U.S. Pub. No. 2018/0132853 on May 17, 2018, may be combined will be apparent to those of ordinary skill in the art.

It should also be understood that the teachings above may be readily combined with the teachings of U.S. patent application Ser. No. 15/350,593, entitled "Atraumatic Stapling Head Features for Circular Surgical Stapler," filed Nov. 14, 2016, issued as U.S. Pat. No. 10,542,981 on Jan. 28, 2020, the disclosure of which is incorporated by reference herein. Various suitable ways in which the teachings herein and the teachings of U.S. patent application Ser. No. 15/350,593, filed on Nov. 14, 2016, issued as U.S. Pat. No. 10,542,981, on Jan. 28, 2020, may be combined will be apparent to those of ordinary skill in the art.

It should also be understood that the teachings above may be readily combined with the teachings of U.S. patent application Ser. No. 15/350,621, entitled "Staple Forming Pocket Configurations for Circular Surgical Stapler Anvil," filed Nov. 14, 2016, published as U.S. Pub. No. 2018/0132849 on May 17, 2018, the disclosure of which is incorporated by reference herein. Various suitable ways in which the teachings herein and the teachings of U.S. patent application Ser. No. 15/350,621, filed Nov. 14, 2016, published as U.S. Pub. No. 2018/0132849 on May 17, 2018, may be combined will be apparent to those of ordinary skill in the art.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat.

No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly has a distal end;
   (c) a stapling head assembly located at the distal end of the shaft assembly, wherein the stapling head assembly comprises:
      (i) a deck member, wherein the deck member comprises:
         (A) a first deck surface,
         (B) a second deck surface, wherein the second deck surface is recessed relative to the first deck surface,
         (C) an outer annular array of staple openings, wherein the outer annular array is formed through the first and second deck surfaces,
         (D) an inner annular array of staple openings, wherein the inner annular array is formed through the first and second deck surfaces, and
         (E) a plurality of stand-off features extending distally from the second deck surface,
      (ii) a plurality of staples, and
      (iii) a driver operable to drive the staples through the staple openings; and
   (d) an anvil, wherein the anvil is operable to compress tissue against the deck surface.

2. The apparatus of claim 1, wherein each stand-off feature at least partially encompasses an end of a corresponding staple opening of the outer annular array of staple openings.

3. The apparatus of claim 1, wherein each stand-off feature at least partially encompasses an end of a corresponding staple opening of the inner annular array of staple openings.

4. The apparatus of claim 1, wherein each stand-off feature comprises an outer wall portion and an inner wall portion, wherein the outer wall portion at least partially encompasses an end of a corresponding staple opening of the outer annular array of staple openings, wherein the inner wall portion at least partially encompasses an end of a corresponding staple opening of the inner annular array of staple openings.

5. The apparatus of claim 4, wherein the outer wall portion and the inner wall portion of each stand-off feature interconnect to define a respective zig-zag configuration.

6. The apparatus of claim 1, wherein each stand-off feature has a rounded outer edge having a curvature.

7. The apparatus of claim 6, wherein the first deck surface has a rounded outer edge, wherein the rounded outer edge of the first deck surface has the same curvature as the curvature of the rounded outer edges of the stand-off features.

8. The apparatus of claim 1, wherein each stand-off feature has an upper end located along a plane, wherein the first deck surface is coplanar with the plane.

9. The apparatus of claim 1, wherein the deck member further includes a step-down transition from the first deck surface to the second deck surface.

10. The apparatus of claim 1, wherein the deck member defines a first angular region and a second angular region, wherein the first deck surface extends along only the first angular region, wherein the second deck surface extends along only the second angular region.

11. The apparatus of claim 10, wherein the first angular region extends along an angular range between approximately 30° and approximately 90° of a circumference of the deck member.

12. The apparatus of claim 10, wherein the shaft assembly comprises a curved section including an inner curve and an outer curve.

13. The apparatus of claim 12, wherein the first angular region is angularly positioned to correspond with the outer curve, wherein the second angular region is angularly positioned to correspond with the inner curve.

14. The apparatus of claim 1, wherein the first deck surface is flat.

15. The apparatus of claim 1, wherein the deck member further comprises an inner annular wall extending distally from the second deck surface.

16. The apparatus of claim 15, wherein the inner annular wall has a distal end that is coplanar with at least a portion of the first deck surface.

17. The apparatus of claim 15, wherein the inner annular wall is spaced inwardly from the stand-off features such that a recess is defined between the inner annular wall and the stand-off features.

18. An apparatus comprising a stapling head assembly, wherein the stapling head assembly comprises:
(a) an annular deck member, wherein the annular deck member comprises:
  (i) a first deck surface extending along a first angular range of the annular deck member,
  (ii) a second deck surface extending along a second angular range of the annular deck member and not along the first angular range, wherein the second deck surface is recessed relative to the first deck surface,
  (iii) an outer annular array of staple openings formed through the first and second deck surfaces,
  (iv) an inner annular array of staple openings formed through the first and second deck surfaces, and
  (v) a plurality of tissue engagement features protruding distally from the second deck surface;
(b) a plurality of staples; and
(c) a driver operable to drive the staples through the staple openings.

19. An apparatus comprising:
(a) a shaft assembly, wherein the shaft assembly comprises:
  (i) a proximal shaft section,
  (ii) a distal shaft section, and
  (iii) a curved shaft section that connects the proximal shaft section with the distal shaft section, wherein the curved shaft section defines an inner shaft curve and an outer shaft curve diametrically opposed from one another across a longitudinal axis of the shaft assembly; and
(b) a stapling head assembly located at the distal end of the shaft assembly, wherein the stapling head assembly comprises:
  (i) a first deck surface having a first angular extent positioned to align with the outer shaft curve of the shaft assembly and not the inner shaft curve,
  (ii) a second deck surface having a second angular extent positioned to align with the inner shaft curve of the shaft assembly and not the outer shaft curve, wherein the second deck surface is recessed relative to the first deck surface,
  (iii) an outer annular array of staple openings formed through the first and second deck surfaces,
  (iv) an inner annular array of staple openings formed through the first and second deck surfaces,
  (v) a plurality of tissue engagement features extending distally from or recessed within the second deck surface,
  (vi) a plurality of staples, and
  (vii) a driver operable to drive the staples through the staple openings.

20. The apparatus of claim 19, wherein the tissue engagement features are not provided on the first deck surface.

* * * * *